(12) United States Patent
Jeung (10) Patent No.: US 8,198,579 B2
(45) Date of Patent: Jun. 12, 2012

(54) SYSTEMS AND METHODS FOR CALIBRATING ALIGNMENT DEVICES

(75) Inventor: Andrew G. Jeung, Mountain View, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1077 days.

(21) Appl. No.: 11/590,075

(22) Filed: Oct. 30, 2006

(65) Prior Publication Data

US 2008/0101669 A1 May 1, 2008

(51) Int. Cl.
G12B 13/00 (2006.01)
(52) U.S. Cl. .................................................. 250/252.1
(58) Field of Classification Search ................. 250/252.1
See application file for complete search history.

(56) References Cited

U.S. PATENT DOCUMENTS

| | | | |
|---|---|---|---|
| 4,296,329 A * | 10/1981 | Mirabella | 250/491.1 |
| 5,774,519 A * | 6/1998 | Lindstrom et al. | 378/18 |
| 6,148,095 A | 11/2000 | Prause et al. | |
| 6,302,580 B1 * | 10/2001 | Dwyer et al. | 378/197 |
| 6,493,574 B1 | 12/2002 | Ehnholm et al. | |
| 6,516,046 B1 | 2/2003 | Frohlich et al. | |
| 6,857,778 B2 | 2/2005 | Mun et al. | |
| 6,888,919 B2 | 5/2005 | Graf | |
| RE38,897 E | 11/2005 | Krenzel | |
| 7,065,393 B2 | 6/2006 | Sati et al. | |
| 2002/0115932 A1 | 8/2002 | Kennedt et al. | |
| 2003/0123614 A1 | 7/2003 | Silver et al. | |
| 2004/0264648 A1 | 12/2004 | Claus et al. | |
| 2005/0084073 A1 | 4/2005 | Seppi et al. | |
| 2005/0094771 A1 | 5/2005 | Basu et al. | |
| 2005/0117708 A1 | 6/2005 | Cho et al. | |
| 2006/0002519 A1 | 1/2006 | Jenkins et al. | |
| 2006/0082774 A1 * | 4/2006 | Buttner et al. | 356/399 |
| 2006/0245628 A1 | 11/2006 | Jeung et al. | |
| 2007/0041508 A1 | 2/2007 | Tubbs | |
| 2008/0240535 A1 | 10/2008 | Frangioni et al. | |

FOREIGN PATENT DOCUMENTS

WO 2005124296 A2 12/2005

OTHER PUBLICATIONS

Non-Final Office Action dated Oct. 20, 2009 for U.S. Appl. No. 11/119,019.

(Continued)

*Primary Examiner* — David Porta
*Assistant Examiner* — Casey Bryant
(74) *Attorney, Agent, or Firm* — Vista IP Law Group, LLP (57) ABSTRACT

A calibration device includes a structure, and a target object that is moveably coupled to the structure, the target object being a physical target towards which an alignment device can be aimed. A calibration device includes a block having a first opening, and a target object that is viewable through the first opening. A method of calibrating an alignment device includes determining a target position associated with a machine, placing a target object at the target position, and adjusting the alignment device using the target object. A calibration device includes a target object, the target object being a physical target towards which an alignment device can be aimed, wherein the target object comprises a first feature for indicating a first orientation of the target object.

25 Claims, 10 Drawing Sheets

OTHER PUBLICATIONS

Beque et al. "Optimization of Geometrical Calibration in Pinhole SPECT", IEEE Transactions on Medical Imaging vol. 24, No. 2, Feb. 2005 pp. 180-190—device fittings over source beams with geometric parameter calibration.

Rizo, et al. "Geometric Calibration Method for Multiple-Head Cone-Beam SPECT System", IEEE Transactions on Nuclear Science, Dec. 1994 vol. 41, No. 6 pp. 2748-2757.

Office Action dated May 12, 2008 for U.S. Appl. No. 11/119,019.

Cho, Y. et al. "Accurate Technique for Complete Geometric Calibration of Cone-Beam Computed Tomography Systems." Medical Physics (Apr. 2005) 32(4):968-983.

Fahrig, R. and D.W. Holdsworth "Three-Dimensional Computed Tomographic Reconstruction Using a C-arm Mounted XRII: Image-Based Correction of Gantry Motion Nonidealities" Medical Physics (Jan. 2000) 27(1):30-38.

Noo, F. et al. "Analytic Method Based on Identification of Ellipse Parameters for Scanner Calibration in Cone-Beam Tomography." Phys. Med. Biol. (2000) 45:3489-3508.

Rougée, A. et al. "Geometrical Calibration for 3D X-ray Imaging." SPIE (Sep. 1993) 1897:161-169.

Notice of Allowance dated Apr. 14, 2010 for U.S. Appl. No. 11/119,019.

Navab et al. "Dynamic Geometrical Calibration for 3-D Cerebral Angiography" SPIE (Feb. 1996) 2708: 361-370.

Silver et al. "Determination and Correction of the Wobble of a C-arm gantry" Proc. SPIE 3979, 1459-1468 (2000).

Bani-Hashemi et al. "Cone Beam CT Reconstruction with No Isocentricity Requirement" Med. Phys. 30, 1415 (2003).

Notice of Allowance dated Jul. 23, 2010 for U.S. Appl. No. 11/119,019.

International Search Report for International Application No. PCT/US2007/023021 Dated Jul. 9, 2008.

International Written Opinion for International Application No. PCT/US2007/023021 Dated Jul. 9, 2008.

* cited by examiner

SYSTEMS AND METHODS FOR CALIBRATING ALIGNMENT DEVICES

RELATED APPLICATION DATA

This application is related to U.S. patent application Ser. No. 11/119,019, filed on Apr. 29, 2005, the entire disclosure of which is expressly incorporated by reference herein.

FIELD

This application relates generally to alignment devices for use with a medical device, and more specifically, to systems and methods for calibrating such alignment devices.

BACKGROUND

When using a radiation device, such as a radiation treatment machine or a radiation imaging machine, the location of the isocenter, or the point in space where the radiation beams from different gantry angles converge, needs to be known and verified precisely. In existing systems, the isocenter of a radiation machine is identified by a set of fan-beam room lasers, each of which defines an orthogonal plane. These planes intersect the isocenter to identify that position. A common installation of a laser alignment system has four laser source points: two wall lasers, which project laser beams on either side of the patient, and two ceiling lasers (one of which being directly over the gantry). Alignment of these lasers involves adjusting the lasers until their respective laser beams intersect the isocenter, and such procedure is typically done during installation of the radiation machine. However, over time, the intersection point of the laser beams may deviate from the true isocenter position. As such, re-alignment of the lasers are required to be performed periodically.

Laser alignment is a specialized task that is difficult and time consuming to perform, and requires the skills of experienced service personnel. As such, it may be desirable to provide a system and method that would allow calibration of the alignment device to be performed conveniently, accurately, and efficiently.

SUMMARY

In accordance with some embodiments, a calibration device includes a structure, and a target object that is moveably coupled to the structure, the target object being a physical target towards which an alignment device can be aimed.

In accordance with other embodiments, a calibration device includes a block having a first opening, and a target object that is viewable through the first opening.

In accordance with other embodiments, a method of calibrating an alignment device includes determining a target position associated with a machine, placing a target object at the target position, and adjusting the alignment device using the target object.

In accordance with other embodiments, a calibration device includes a target object, the target object being a physical target towards which an alignment device can be aimed, wherein the target object comprises a first feature for indicating a first orientation of the target object.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments, in which similar elements are referred to by common reference numerals. In order to better appreciate how advantages and objects of the embodiments are obtained, a more particular description of the embodiments will be illustrated in the accompanying drawings.

DETAILED DESCRIPTION OF THE EMBODIMENTS

Various embodiments are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments.

Radiation System

Figure 1:
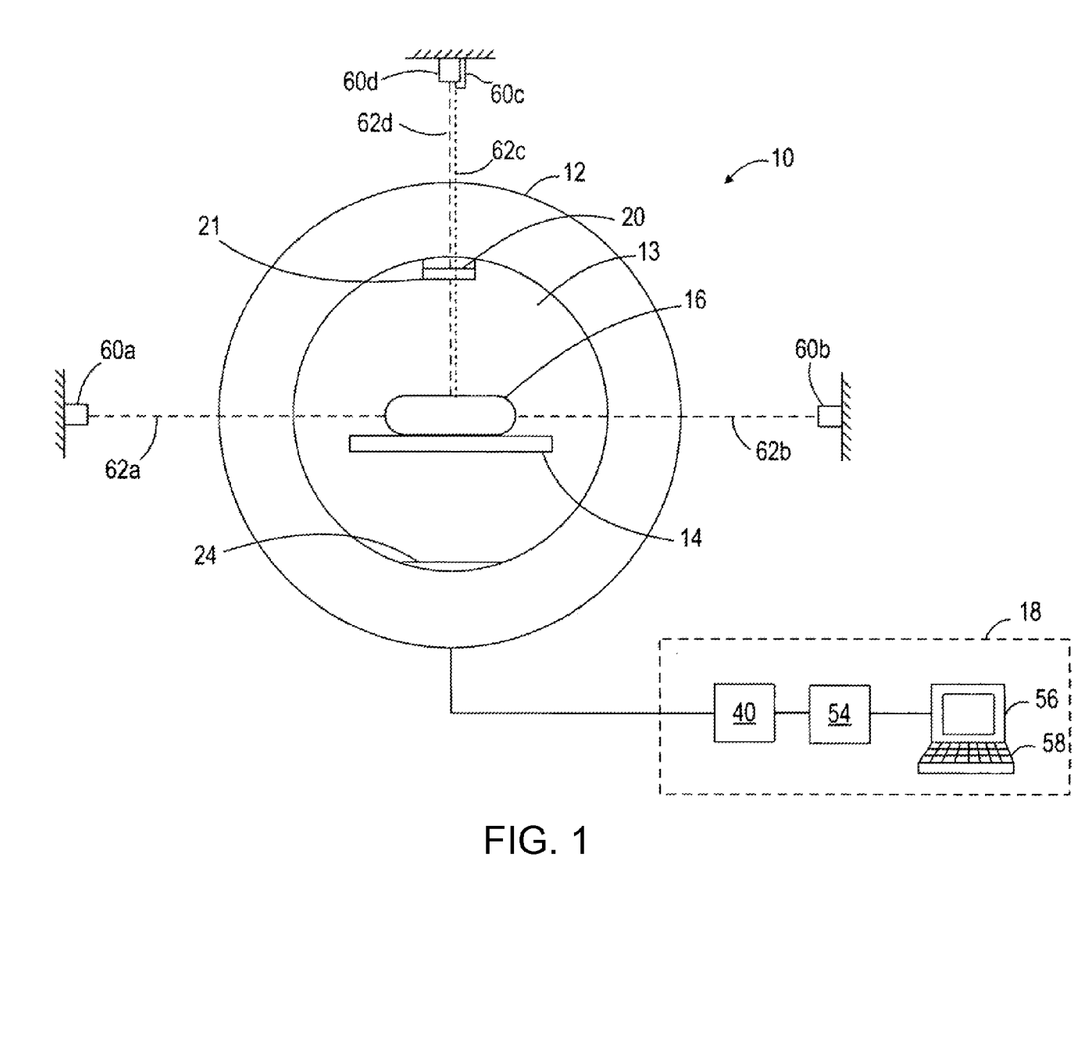
FIG. 1 illustrates a radiation system and alignment lasers.

FIG. 1 illustrates a radiation system 10. The system 10 includes a gantry 12 having an opening (or bore) 13, a patient support 14 for supporting a patient 16, and a control system 18 for controlling an operation of the gantry 12. In the illustrated embodiments, the gantry 12 has a slip-ring configuration (donut shape). Alternatively, the gantry 12 can have other configurations, such as a C-arm configuration. The system 10 also includes a radiation source (e.g., x-ray source) 20 that projects a beam of radiation towards the patient 16, and a collimator 21 for changing a shape of the beam. The system 10 also includes a detector 24 on an opposite side of the gantry 12, which in some cases, may be used to receive radiation exiting from the patient 16, and generate image(s) using the received radiation. The detector 24 has a plurality of sensor elements configured for sensing a x-ray that passes through the patient 16. Each sensor element generates an electrical signal representative of an intensity of the x-ray beam as it passes through the patient 16. In other embodiments, the system 10 does not include the detector 24.

In the illustrated embodiments, the radiation source 20 is a treatment radiation source for providing treatment energy. In other embodiments, the radiation source 20 may be a diagnostic radiation source for providing diagnostic energy (e.g., energy that is suitable for generating an image). In further embodiments, the radiation source 20 can be configured to selectively provide treatment energy and diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIO-THERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003.

The control system 18 includes a processor 54, such as a computer processor, coupled to a source rotation control 40. The control system 18 may also include a monitor 56 for displaying data and an input device 58, such as a keyboard or a mouse, for inputting data. During a scan to acquire x-ray projection data (e.g., cone beam CT image data), the source 20 rotates about the patient 16. The rotation of the source 20 and the operation of the radiation source 20 are controlled by the source rotation control 40, which provides power and timing signals to the radiation source 20 and controls a rotational speed and position of the source 20 based on signals received from the processor 54. Although the control 40 is shown as a separate component from the gantry 12 and the processor 54, in alternative embodiments, the control 40 can be a part of the gantry 12 or the processor 54.

During a radiation procedure, the radiation source 20 generates and directs an x-ray beam towards the patient 16, while the detector 24 measures the x-ray absorption at a plurality of transmission paths defined by the x-ray beam during the process. The detector 24 produces a voltage proportional to the intensity of incident x-rays, and the voltage is read and digitized for subsequent processing in a computer. After image data at different gantry angles have been collected, the collected data are processed for reconstruction of a matrix (CT image), which constitutes a depiction of a density function of the bodily section being examined. By considering one or more of such sections, a skilled diagnostician can often diagnose various bodily ailments. In some cases, the one or more sections can also be used to perform treatment planning.

As shown in the figure, four lasers 60a-60d are positioned adjacent to the system 10. The lasers 60a-60d are configured to generate respective laser beams 62a-62d, which may be used to align the patient 16 at a desired location. In the illustrated embodiments, lasers 60a, 60b are configured to generate and project laser beams 62a, 62b from opposite sides of the patient 16, laser 60c is configured to generate and project laser beam 62c from above the patient 16, and laser 60d is configured to generate and project laser beam 62d downwardly at an angle onto the patient 16. In other embodiments, the lasers 60 may be configured to project the laser beams 62 from other directions. Each laser 60 may be mounted to any structure, such as a wall, a ceiling, a patient support, or another device. Although four lasers 60 are shown, in other embodiments, more or less than four lasers 60 may be used. For example, in other embodiments, only lasers 60a-60c are used.

Figure 2:
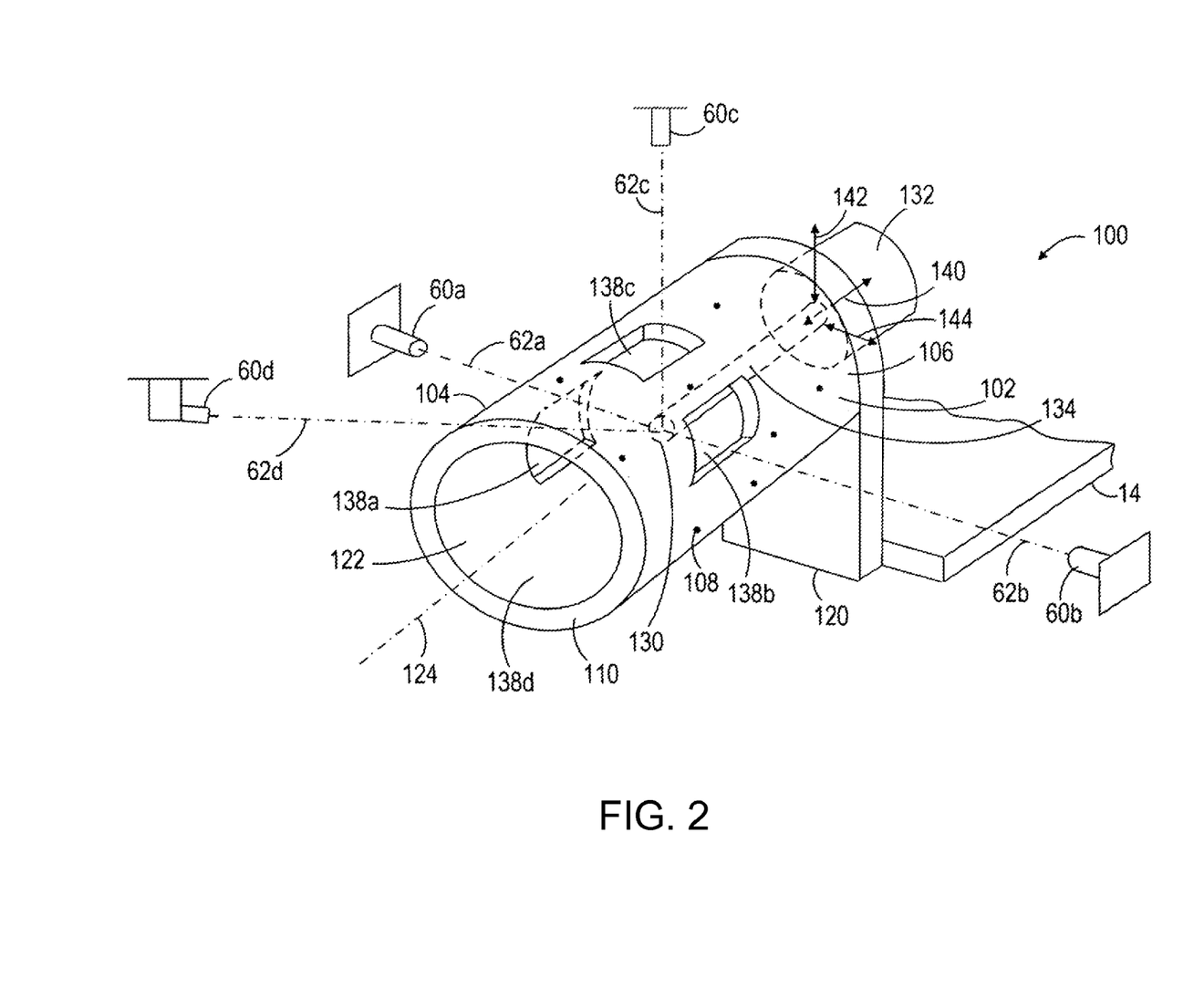
FIG. 2 illustrates a device for use in a procedure to adjust the alignment lasers of FIG. 1 in accordance with some embodiments.

FIG. 2 illustrates a calibration device 100 that may be used to configure the lasers 60 of FIG. 1 in accordance with some embodiments. The device 100 includes a tubular structure 102 having a first end 104 and a second end 106, and a plurality of radio-opaque markers 108 embedded within a wall 110 of the tubular structure 102. Alternatively, instead of embedding the markers 108 within the wall 110, the markers 108 can be secured to a surface (e.g., an interior surface or an exterior surface) of the tubular structure 102. The markers 108 may be permanently secured to the structure 102. In other embodiments, the markers 108 may be detachably secured to the structure 102. For example, each of the markers 108 may have a securing mechanism, such as a Velcro, a pin, a clamp, a screw, a bolt, a clip, or the like, for securing the marker 108 to the structure 102. In some cases, the structure 102 may have a plurality of openings for allowing the markers 108 to be secured to the structure 102.

The tubular structure 102 has a circular cross-sectional shape. In the illustrated embodiments, the tubular structure 102 has a length along its axis that is between 4 and 18 inches, and preferably, 9 inches, and a cross-sectional dimension that is between 4 and 8 inches, and preferably, 9 inches, with the wall having a thickness that is between 0.2 inch to 2 inches, and preferably, 0.5 inch. In other embodiments, the tubular structure 102 can have other cross-sectional shapes (such as an elliptical shape, a square, a rectangular, or other customized shapes) and/or dimensions. In some embodiments, the structure 102 is dimensioned such that its ends 104, 106 are not visible in an image frame generated by the system 10.

In the illustrated embodiments, each of the markers 108 is a tungsten-carbide BB (sphere) having a cross-sectional dimension that is between 2 mm to 4 mm. In other embodiments, the markers 108 can be other radio-opaque objects, and can have other cross-sectional dimensions. In further embodiments, the markers 108 are not radio-opaque, but are made from a material that allows them to be distinguishable from the rest of an image. In other embodiments, the markers 108 can have other shapes, such as an elongated configuration. Also, in other embodiments, instead of all the markers 108 having a similar cross-sectional dimension, the markers 108 can have different dimensions. As shown in the figure, the device 100 includes sixteen markers 108. In other embodiments, the device 100 can have fewer or more than sixteen markers 108. For example, the device 100 can have four markers 108 in some embodiments. In some embodiments, the markers 108 are positioned such that as the gantry 12 rotates, all of the markers 108 can be seen in the detector 24 and none of the markers 108 overlap. In the illustrated embodiments, the markers 108 are positioned relative to each other such that they collectively form an irregular pattern. Alternatively, the markers 108 collectively form a regular pattern, such as a spiral, or a portion of a geometric profile. As another example of a regular pattern, a first group of the markers 108 can form a first profile that is a mirror image, or a reverse mirror image, of a second profile formed by a second group of the markers 108.

In the illustrated embodiments, the device 100 further includes a mounting mechanism 120 configured for securing the device 100 to the patient support 14. The mounting mechanism 120 is in a form of a plate which attaches to a set of hooks (not shown) on the patient support 14. Alternatively, the mounting mechanism 120 can have other shapes and/or configurations. Also, in other embodiments, the device 100 does not include the mounting mechanism 120. In such cases, a separate connection may be provided for securing the device 100 relative to the patient support 14.

In the illustrated embodiments, the device 100 further includes a target object 130 located within a lumen 122 of the tubular structure 102, a positioner 132, and a rod 134 coupling the target object 130 to the positioner 132. The positioner 132 is configured to position the target object 130 at a desired location, such as the isocenter of the radiation system 10. In the illustrated embodiments, the positioner 132 is configured to translate the target object 130 in three orthogonal directions 140, 142, 144. In other embodiments, the positioner 132 may be configured to translate the target object 130 in less than three directions (e.g., one or two directions), and the directions of translation need not be orthogonal relative to each other.

In the illustrated embodiments, the structure 102 includes a plurality of openings 138 at the wall 110 of the structure 102. The target object 130 is viewable through the openings 138 during use. In the illustrated embodiments, the device 100 includes four openings 138a-138d, which allow the target object 130 to be viewed from different angles. In other embodiments, the device 100 may include other numbers of openings 138. For example, in other embodiments, the end 104 of the structure 102 may have a closed end, in which case, the device 100 will not have the opening 138d. In further embodiments, the structure 102 may not include the opening 138c. In other embodiments, the location of the openings 138 may be different from that shown in the example. In still further embodiments, the structure 102 may not include any opening 138 at all. In such cases, at least portion(s) of the structure 102 may be made of an optically transparent material, which allows the target object 130 to be viewed from outside the structure 102. The target object 130 may have size and/or shape that is different from the markers 108. Alternatively, the target object 130 may have the same size and shape as the markers 108.

Figure 3:
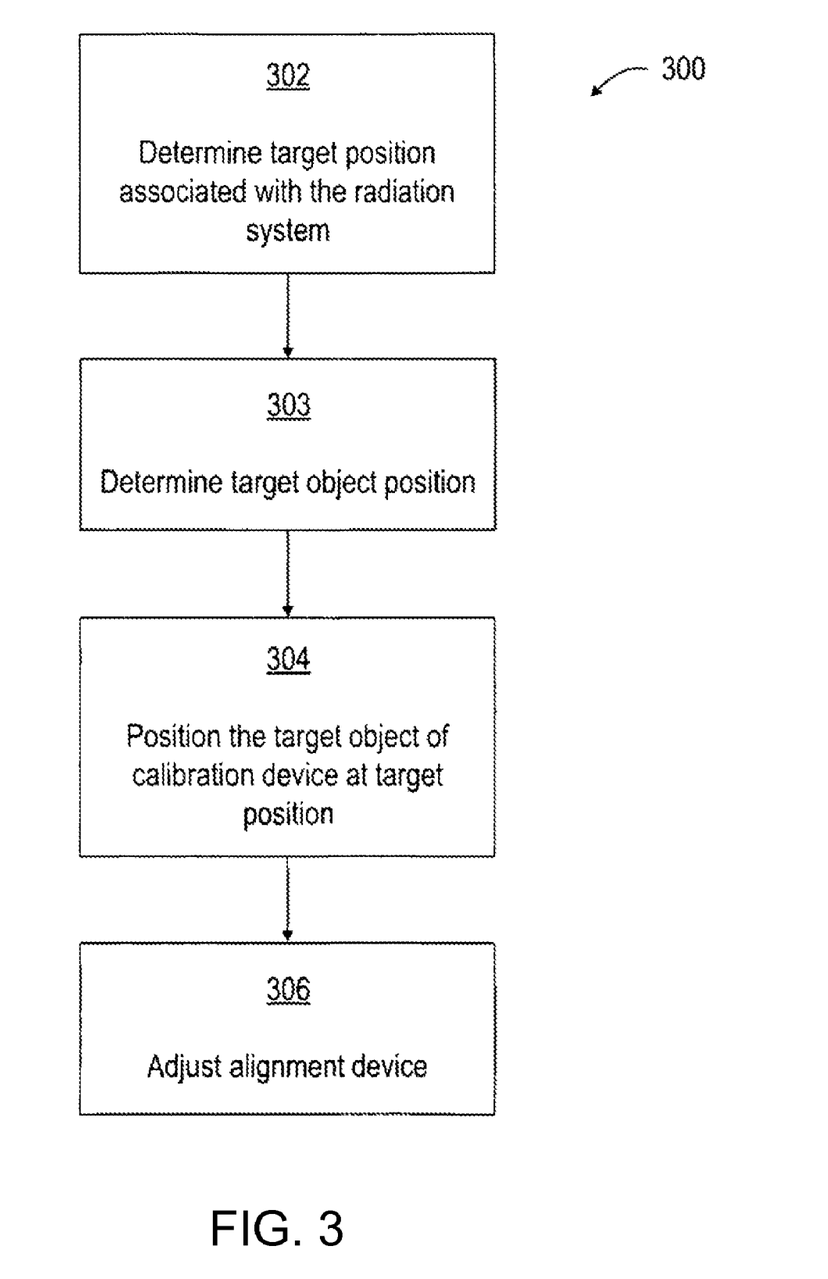
FIG. 3 illustrates a method for adjusting alignment laser(s) in accordance with some embodiments.

FIG. 3 illustrates a method 300 for configuring the alignment lasers 60 of FIG. 1 in accordance with some embodiments. First, a target position associated with the radiation system 10 is determined (Step 302). In the illustrated embodiments, the target position associated with the radiation system 10 may be the isocenter of the radiation system 10. As used in this specification, the term "isocenter" refers to a point at which radiation beams from different gantry angles intersect. In other embodiments, the target position may be other locations, such as a location prescribed by a user.

Next, the position of the target object 130 is determined (Step 303), and the target object 130 is then positioned from the determined target object 130 position to the determined the target position (Step 304). In the illustrated embodiments, the target object 130 is placed at the target position based on the offset between the target position and the determined position of the target object 130. For example, the target object 130 may be moved in the direction of the offset and by the amount of the offset, thereby placing the target object 130 at the target position (e.g., the isocenter of the system 10).

Figure 4:
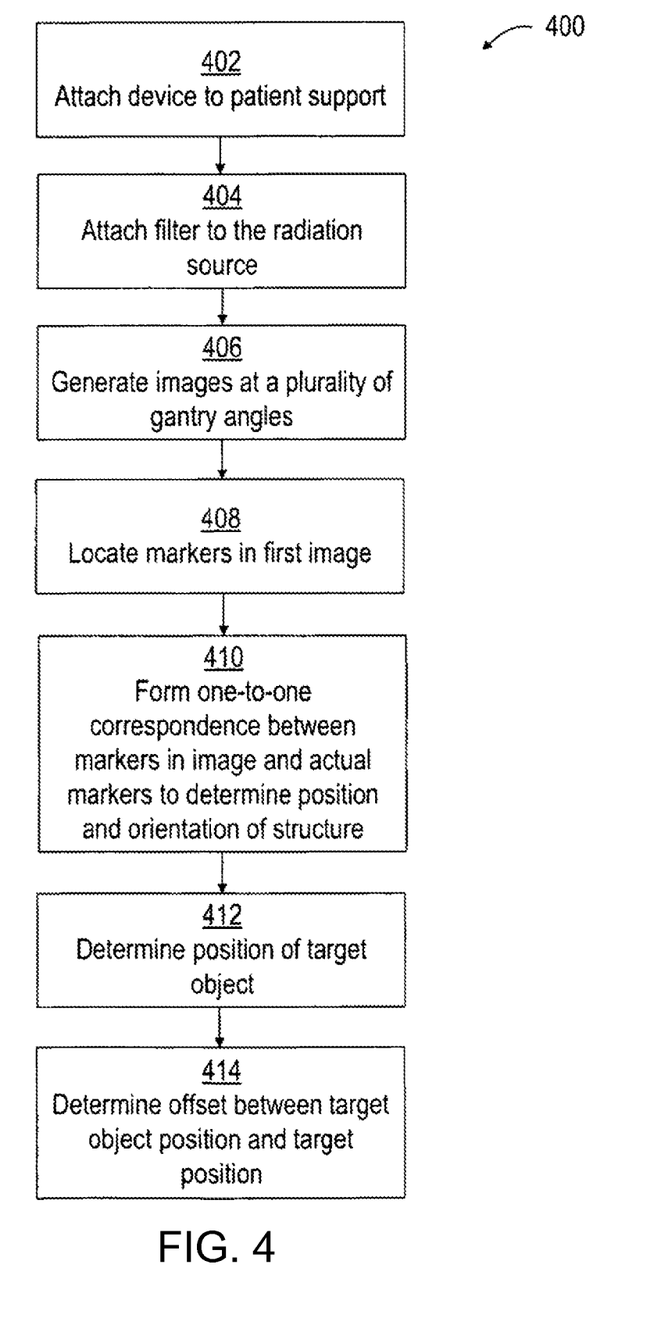
FIG. 4 illustrates a method for performing a part of the method of FIG. 3 in accordance with some embodiments.
Figure 5:
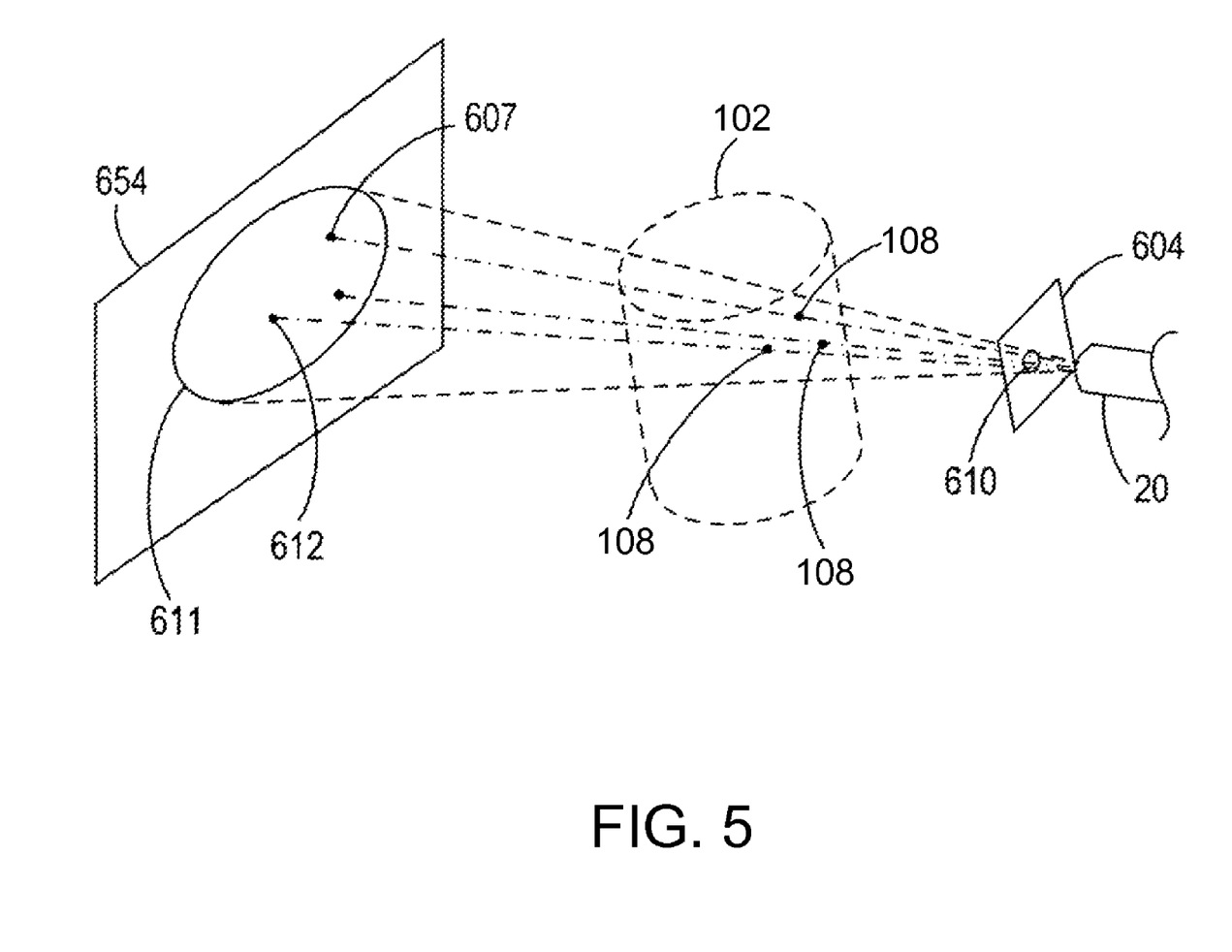
FIG. 5 is a diagram illustrating an example of an image frame that includes an image of a filter opening.

Various techniques may be used to determine the position of the target position, the position of the target object 130, and the offset between the target position and the target object 130 position. FIGS. 4 and 5 illustrate a method 400 that may be used for such purposes in accordance with some embodiments. First, the calibration device 100 is secured to the system 10 (Step 402). In some cases, although not required, it may be desirable to place the calibration device 100 such that a reference location (e.g., the location of the target object 130) of the calibration device 100 is located at, or coincides with, an expected/estimated isocenter position of the system 10. In some embodiments, the device 100 is secured in a known fixed position, and is oriented such that the axis 124 of the device 100 is substantially parallel to (e.g., within 5° from) a rotational axis of the source 20. In other embodiments, the device 100 may be secured in other orientation relative to the gantry 12 or relative to the patient support 14.

Next, a filter 604 having an opening 610 is then secured between the radiation source 20 and the calibration device 100 (Step 404). In one implementation, the filter 604 is secured in front of the radiation source 20.

Next, the system 10 is used to generate images at a plurality of gantry angles (Step 406). In the illustrated embodiments, the source 20 is rotated at an increment in the range of ½° to 5°, and more preferably of 3°, between the acquisition of each image. Alternatively, the source 20 can be rotated at other increment of gantry angles. The generated image will include images of the markers 108.

Next, the processor 54 determines the positions of the markers 108 in the first generated image (e.g., the image generated at any one of the gantry angles) (Step 408). In the illustrated embodiments, the processor 54 is configured (e.g., programmed or designed) to perform a background subtraction of the image frame to remove undesirable background details. For example, a rolling ball technique (commonly used in the field of gel electrophoresis) may be used to perform the background subtraction. In the rolling ball technique, portion(s) of the generated image-having a concavity in the grayscale value less than a prescribed threshold is removed. In other embodiments, the process 400 does not include the step of performing background subtraction. After the background subtraction has been performed, the processor 54 then converts the image frame to a binary image by thresholding. The threshold level can be set by calculating the number of pixels expected in the foreground, or by entropy thresholding. The binary image can then be analyzed by the processor 54 to determine the positions of the markers 108 in the generated image. In other embodiments, other techniques known in the art of image processing can also be used to determine the positions of the markers 108 in the generated image.

Next, the processor 54 associates, or forms a one-to-one correspondence, between the projections of each marker 108 in the first generated image and the markers 108 themselves (Step 410). In the illustrated embodiments, the processor 54 forms this correspondence by determining a possible position and orientation of the structure 102 that could produce the arrangement of markers 108 in the image. Various techniques can be employed for such purpose. For example, the processor 54 can be configured to make an initial estimate of the position of the structure 102, and then attempt to match at least a subset of the projected positions of the markers 108 (that correspond with the estimated position of the structure 102) with at least a subset of the positions of the markers 108 in the actual image. For example, if the generated image contains six markers 108, the processor 54 can be configured to select a subset (e.g., four) of markers 108 in the image, and then attempts to match the four markers 108 with four estimated projected location of the markers 108 that are associated with the estimated position of the structure 102. Alternatively, the processor 54 can be configured to use all of the markers 108 in the image to determine a possible orientation of the structure 102. In some cases, if an initial estimate of the position of the structure 102 cannot be made, an algorithm can be employed in which all possible associations between sets of markers 108 are attempted, with certain obviously incorrect associations eliminated to improve efficiency. Once a match has been found, the estimated position of the structure 102 is then determined to be the position of the structure 102 at the first gantry angle.

In some embodiments, the processor 54 may determine the positions of the markers 108 in one or more additional images in the set generated in step 406, and use such determined positions to verify the determined position of the structure 102.

In some embodiments, the device 100 can be designed to have a certain size, and the number and distribution of markers 108 can be selected such that the processor 54 can determine the position of the structure 102 even if a portion of the structure 102 is outside the image frame. This can be accomplished as long as a subset (e.g., at least four, and preferably, six) of the markers 108 can be detected in the image frame, thereby allowing the processor 54 to determine a position of the structure 102 of the device 100 by associating the subset of markers 108 with a possible orientation of the structure 102 of the device 100.

Because the opening 610 of the filter 604 allows a portion of the generated radiation to pass therethrough, the generated images 654 will each have an image of the filter opening 610. For the case in which the opening 610 is circular, each of the generated images 654 will have an image 611 that corresponds with the opening 610 of the filter 604 (FIG. 5). In the illustrated embodiments, because the filter opening 610 is circular, the image 611 is also circular, with a center 612 of the image 611 indicating a center of a radiation beam (or a center of the radiation source 20). In some cases, the isocenter of the system 10 may be determined by obtaining a plurality of the images 611 at different gantry angles, and determining the intersection of lines (e.g., central beam axes), wherein each line is connected from a respective center 612 of image 611 to the source 20 location at the respective gantry angle. In such cases, the determined intersection is considered as the isocenter of the system 10. Alternatively, the isocenter of the system 10 may be determined by determining the intersection of normals that extend from the respective centers 612 of the images 611. As shown in FIG. 5, because the projection image 611 of the filter opening 610 is larger than an image 607 of each of the markers 108, and because the projection image 611 will appear brighter than the marker images 607, the projection image 611 (and therefore, the center of the radiation source 20) can be determined by the processor 54 without interfering with a tracking of the markers 108.

Next, the position of the target object 130 is determined (Step 412). In the illustrated embodiments, the initial position of the target object 130 relative to the structure 102 is known. As such, the target object 130 position (e.g., relative to a reference coordinate) may be determined (e.g., by the processor 54) using the determined position of the structure 102 (in the reference coordinate) and the known position of the target object 130 relative to the structure 102. The reference coordinate may be one that is associated with the system 10, the patient support 14, or other structures. In some cases, the reference coordinate may be user defined. In other embodiments, if the position of the structure 102 is calculated or expressed in step 410 as the coordinate of the target object 130, then step 412 is not required.

After the position of the target position and the position of the target object 130 are determined, the processor 54 then determines the offset between the target object 130 position and the target position (Step 414).

It should be noted that instead of the technique described, other techniques may be used to determine the isocenter, the position of the structure 102, and the position of the target object 130. For example, techniques for determining the isocenter of a radiation system and a position of a calibration device, such as those described in U.S. patent application Ser. No. 11/119,019 referenced herein, may be used. Also, in other embodiments, the isocenter location, the position of the structure 102, and/or the position of the target object 130 may be determined manually, such as by performing physical measurement(s).

Returning to FIG. 3, in some embodiments, the positioning of the target object 130 (Step 304) may be accomplished using the positioner 132. In some embodiments, the positioner 132 is coupled to the processor (e.g., the processor 54) that determines the offset between the target object 130 and the isocenter. In such cases, the processor may be configured to transmit a signal to cause the positioner 132 to position the target object 130 at the isocenter based on the determined offset.

After the target object 130 has been placed at the target position (the isocenter in the example) associated with the system 10, the alignment lasers 60 can then be calibrated (adjusted) such that the laser beams 62 intersect the target object 130 (Step 306). For example, the lasers 60 can be adjusted by changing their positions and orientations. In the illustrated embodiments, the plurality of openings 138 allows a user to determine whether the laser beams 62 intersect the target object 130 while the lasers 60 are being adjusted.

As illustrated in the above embodiments, the calibration device 100 is advantageous in that it provides a target object 130 for allowing the lasers 60 to be aimed, thereby making it convenient for a user to adjust the lasers 60. In addition, the above described technique allows a mathematical data related to the determined isocenter of the system 10 to be related to a physical target to which the lasers could be aligned.

Although particular embodiments of the method 300/400 has been described, the scope of the invention should not be so limited. In other embodiments, the method 300/400 does not include all of the steps. Also, in other embodiments, the order of the steps in the method 300/400 can be different from that described previously. In addition, in other embodiments, one or more steps in the method 300/400 can be further divided into sub-steps. In further embodiments, one or more steps in the method 300/400 can be combined with other step(s).

Figure 6:
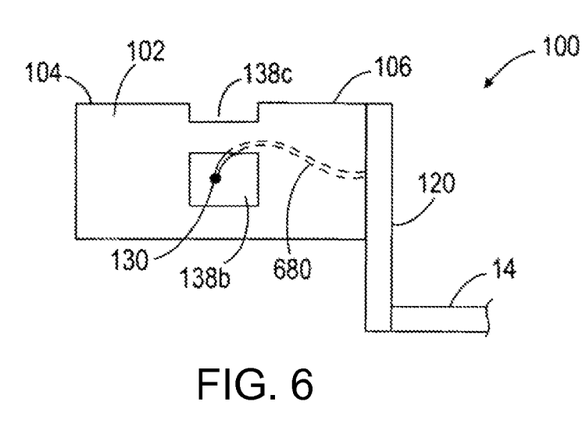
FIGS. 6-7 illustrate variations of the device of FIG. 2 in accordance with other embodiments.

In the above embodiments, the positioning of the target object 130 is performed automatically using the positioner 132. In other embodiments, the device 100 may not include the positioner 132. FIG. 6 illustrates a variation of the device 100 of FIG. 2 in which the positioner 132 is not included. In the illustrated embodiments, the target object 130 of the device 100 is coupled to the structure 120 via a bendable member 680. Alternatively, the target object 130 may be coupled, via the member 680, to other locations of the device 100, such as an interior wall of the device 100. The bendable member 680 may be made from a malleable material that allows the member 680 to be bent. In other embodiments, the member 680 may include a plurality of sub-members that are linked together using rotatable connections (e.g., hinges), thereby allowing the member 680 to be bent. During use, the bendable member 680 may be bent manually to place the target object 130 at a desired position (e.g., the isocenter of the system 10).

Figure 7:
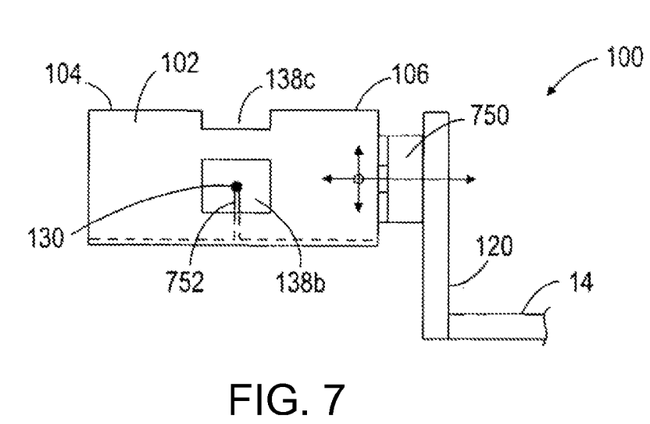

In the above embodiments, the structure 102 is fixedly coupled to the patient support 14. However, in other embodiments, the structure 102 may be moveably coupled to the patient support 14 or another device. FIG. 7 illustrates a variation of the calibration device 100, wherein the structure 102 is moveably coupled to the structure 120. In the illustrated embodiments, the structure 102 is coupled to the positioner 750, which controls the position of the structure 102. The positioner 750 is configured to translate the structure 102 in three orthogonal directions. Alternatively, the positioner 750 may be configured to translate the structure 102 in different directions that are not orthogonal relative to each other. In further embodiments, the positioner 750 may be configured to translate the structure 102 in less than three directions.

As shown in the figure, the target object 130 is coupled to the structure 102 via a coupling member 752, which may be a rigid rod, or a bendable member. In some cases, if the member 752 is bendable, such feature may allow the relative distance between the target object 130 and the structure 120 to be calibrated. During use, the positioner 750 may be used to position the target object 130 at a desired position (e.g., the isocenter of the system 10).

In the above embodiments, the target object 130 has a spherical configuration. However, in any of the embodiments described herein, the target object 130 may have other configurations. For example, in any of the embodiments described herein, the target object 130 may have the configuration shown in FIG. 8. In the illustrated embodiments, the target object 130 includes a plurality of planes 760a-760c, wherein planes 760a, 760b are perpendicular to each other, planes 760a, 760c are perpendicular to each other, and planes 760c, 760b are perpendicular to each other.

Figure 8:
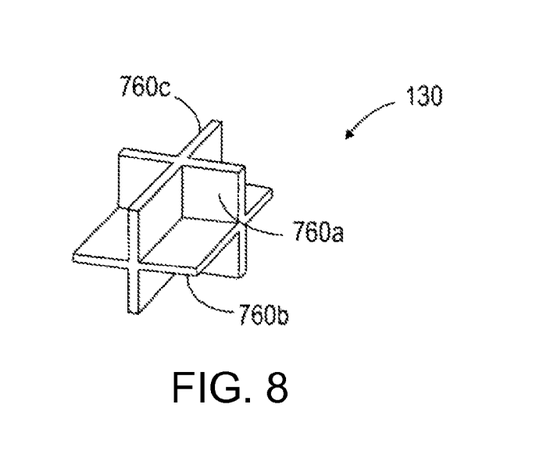
FIG. 8 illustrates a target object in accordance with other embodiments.
Figure 9:
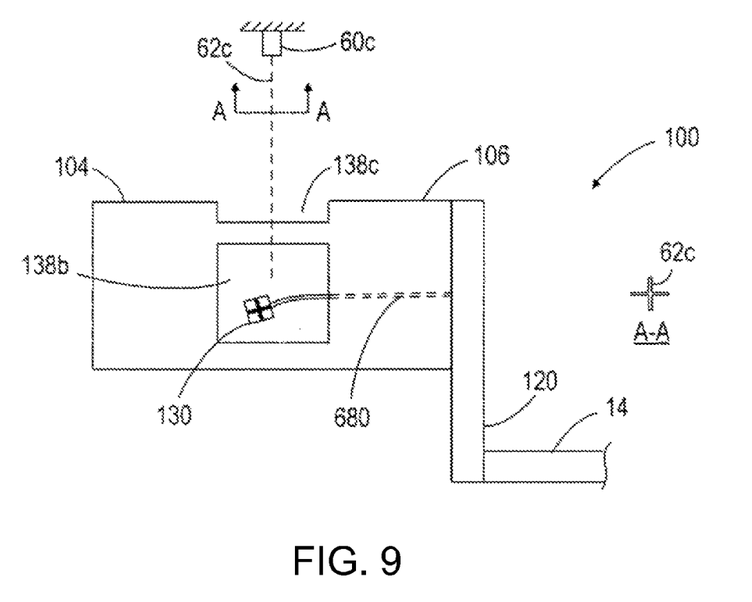
FIGS. 9-12 illustrate variations of the device of FIG. 2 in accordance with other embodiments.

FIG. 9 illustrates the target object 130 of FIG. 8 used in the device 100 of FIG. 6. During use, the member 680 may be bent to place the target object 130 at a desired position (e.g., the isocenter of the system 10). The member 680 may also be bent to rotate the target object 130 such that the planes 760 of the target object 130 are oriented at respective desired orientations (e.g., relative to the structure 102 or to another reference coordinate). For example, the member 680 may be bent such that the plane 760b of the target object 130 is horizontal, and the planes 760a, 760c are vertical. In some cases, the desired orientation of the plane 760b may be one that is parallel to the patient support 14, and the desired orientations of the planes 760a, 760c may be ones that are perpendicular to the plane 760b. The placing of the target object 130 at desired orientations may be assisted by using a lever, or other techniques known in the art. After the target object 130 has been desirably positioned and oriented, the lasers 60 may then be configured to align with the target object 130. In some embodiments, each laser 60 is configured to emit a laser beam that has a "+" cross-sectional shape, as shown in the figure. In such cases, when configuring the laser 60, the laser 60 is positioned such that it is aimed against the target object 130, and is adjusted such that the cross-sectional shape of the laser beam aligns with the cross formed by the planes 760 of the target object 130. For example, the laser 60a may be adjusted such that the cross-sectional shape of its laser beam 62a aligns with the cross formed by the planes 760a, 760b of the target object 130, the laser 60b may be adjusted such that the cross-sectional shape of its laser beam 62b aligns with the cross formed by the planes 760a, 760b of the target object 130, and laser 60c may be adjusted such that the cross-sectional shape of its laser beam 62c aligns with the cross formed by the planes 760a, 760c of the target object 130. If a fourth laser 60d is included, the laser 60d may be adjusted such that the cross-sectional shape of its laser beam 62d aligns with the cross formed by the planes 760b, 760c of the target object 130. In some cases, instead of a cross shape cross section, the fourth laser 60d generates a laser beam that has a single plane only. In such cases, the laser 60d may be adjusted such that the plane of the beam 62d aligns with either plane 760c or plane 760b.

In some cases, the lasers 60 may be adjusted to accomplish one or more of the following objectives: (1) the laser beams 62 all intersect the target object 130, (2) every plane of the laser beams 62 is either coincident or orthogonal to every other plane, and (3) planes of laser beams 62 are orthogonal to the gantry 12 and a vertical axis.

Figure 10:
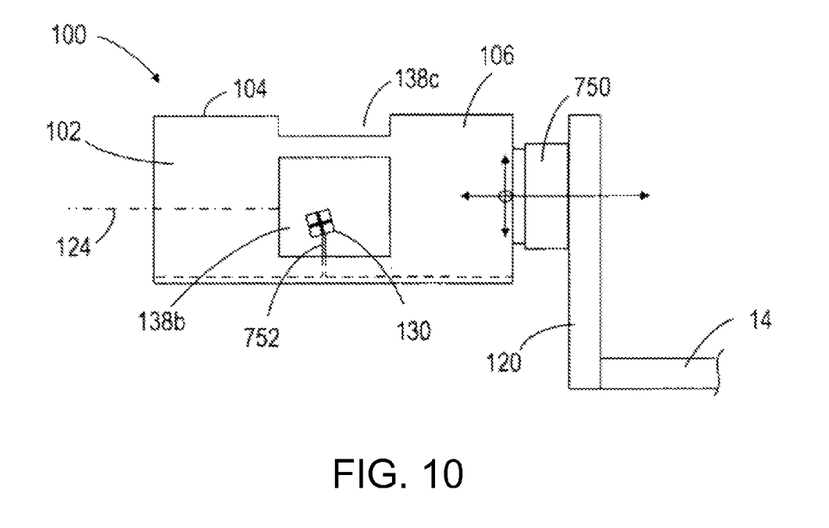

FIG. 10 illustrate the target object 130 of FIG. 8 used in the device of FIG. 7. During use, the positioner 750 may used to place the target object 130 at a desired position (e.g., the isocenter of the system 10) by translating the structure 102. In the embodiments of FIG. 10, the member 752 is bendable, and may be bent manually to rotate the target object 130 such that the planes, 760 of the target object 130 are oriented at respective desired orientations (e.g., relative to the structure 102 or to another reference coordinate). For example, the member 752 may be bent such that the plane 760b of the target object 130 is horizontal, and the planes 760a, 760c are vertical. In some cases, the desired orientation of the plane 760b may be one that is parallel to the patient support 14, and the desired orientations of the planes 760a, 760c may be ones that are perpendicular to the plane 760b. The placing of the target object 130 at desired orientations may be assisted using a lever, or other techniques known in the art. After the target object 130 has been desirably positioned and oriented, the lasers 60 may then be configured to align with the target object 130. In some embodiments, each laser 60 is configured to emit a laser beam that has a "+" cross-sectional shape. In such cases, when configuring the laser 60, the laser 60 is positioned such that it is aimed against the target object 130, and is adjusted such that the cross-sectional shape of the laser beam aligns with the cross formed by the planes 760 of the target object 130. For example, the laser 60a may be adjusted such that the cross-sectional shape of its laser beam 62a aligns with the cross formed by the planes 760a, 760b of the target object 130, the laser 60b may be adjusted such that the cross-sectional shape of its laser beam 62b aligns with the cross formed by the planes 760a, 760b of the target object 130, and laser 60c may be adjusted such that the cross-sectional shape of its laser beam 62c aligns with the cross formed by the planes 760a, 760c of the target object 130. If a fourth laser 60d is included, the laser 60d may be adjusted such that the cross-sectional shape of its laser beam 62d aligns with the cross formed by the planes 760b, 760c of the target object 130. In some cases, instead of a cross shape cross section, the fourth laser 60d generates a laser beam that has a single plane only. In such cases, the laser 60d may be adjusted such that the plane of the beam 62d aligns with either plane 760c or plane 760b.

Alternatively, in the embodiments of FIG. 10, the member 752 may be rigid. In such cases, in additional to being capable of translating the structure 102 (e.g., in three different directions), the positioner 750 may also be one that is capable of rotating the structure 102, thereby placing the target object 130 at desired orientation(s). For example, the positioner 750 may be configured to rotate the structure 102 about the axis 124, thereby changing an orientation of the plane 760b. Alternatively, or additional, the positioner 75 may also be configured to rotate the structure 102 about other axes to thereby change the orientations of the planes 760a, 760c.

It should be noted that the target object 130 may have other configurations in other embodiments, and that it should not be limited to the examples described previously. For example, in other embodiments, the target object 130 may have any shapes, and may include a feature for indicating an orientation of the target object 130. The feature may be, for example, a marking on the target object 130, or alternatively, a portion of the target object 130.

Figure 11:
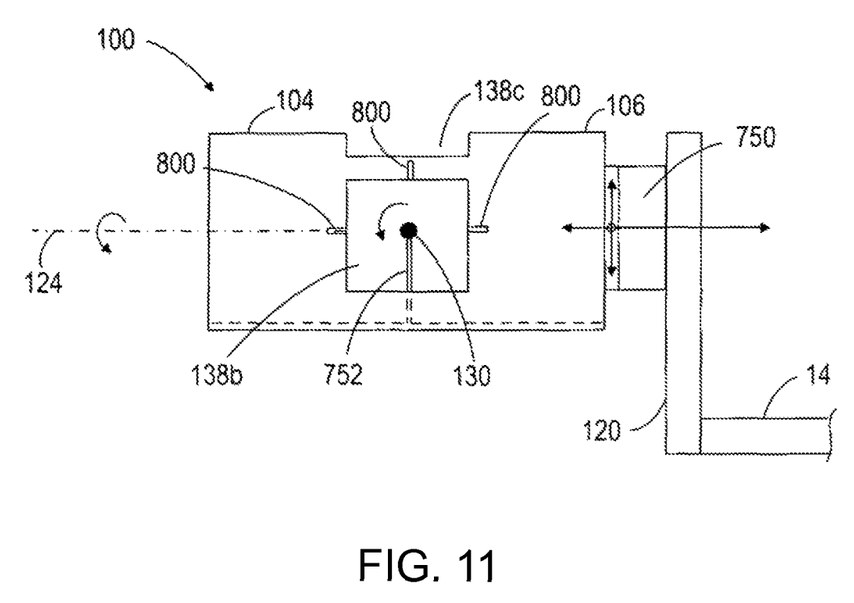

In other embodiments, instead of using the target object 130 to represent desired orientation(s), the structure 102 itself may be used to indicate desired orientation(s) of laser beam(s) 62. FIG. 11 illustrates a variation of the device 100 in which the structure 102 includes markings 800 for use to represent a desired orientation of laser beam 62. In the illustrated embodiments, the positioner 750 may be configured to translate the structure 102 (e.g., in three directions) to thereby place the target object 130 at a desired location (e.g., the isocenter of the system 10), and to rotate the structure 102 (e.g., about three different axes) to orient the structure 102, thereby placing the markings 800 at a desired orientation. During use, after the target object 130 has been desirably placed, and the markings 800 have been desirably oriented, the laser (e.g., laser 60b) is then configured such that its laser beam 62 is aimed towards the target object 130, and the planes (i.e., the ones that form the "+" cross section) of the laser beam 62 are aligned with the markings 800.

Figure 12:
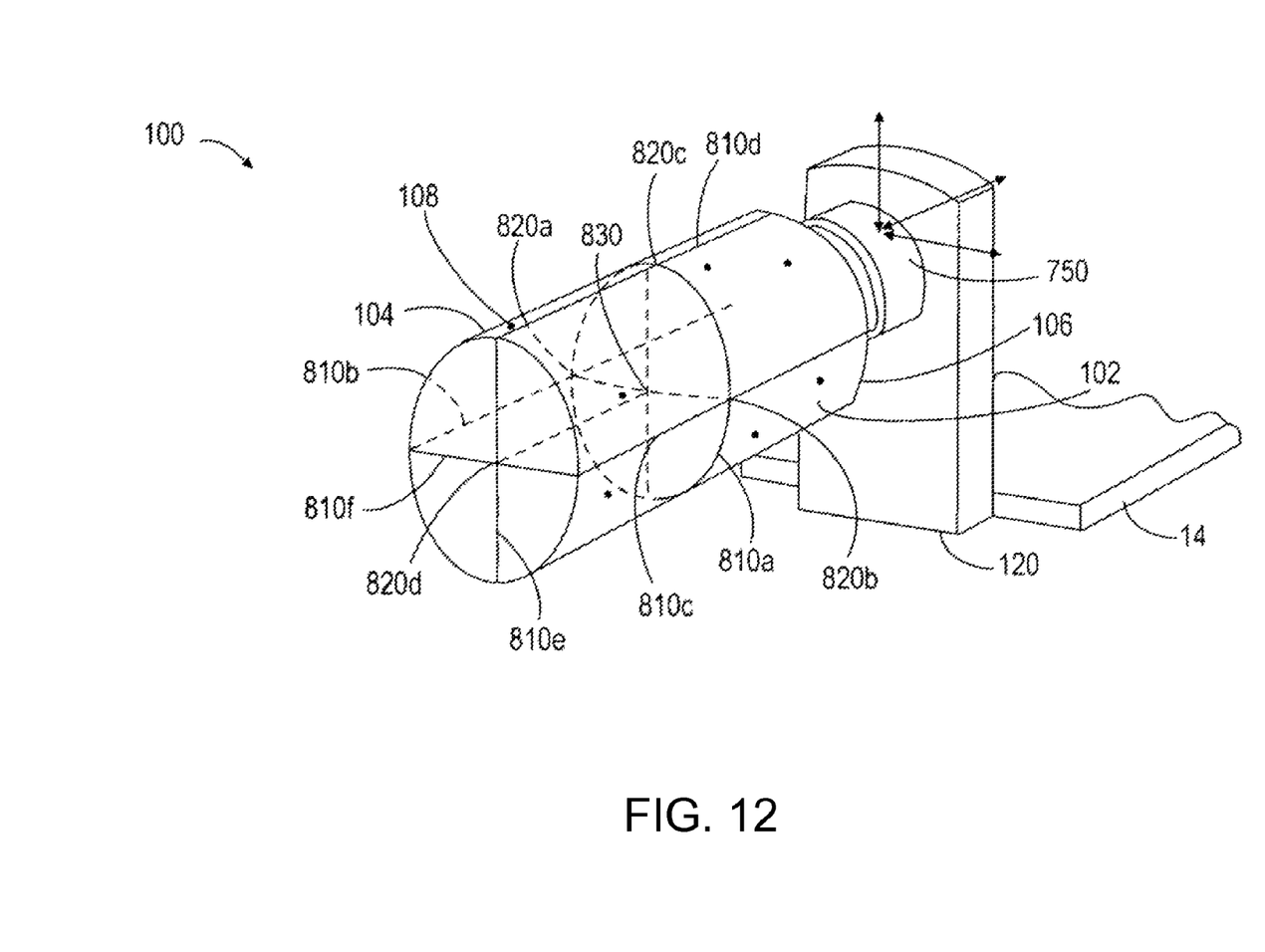

In other embodiments, the device 100 may not include the target object 130. FIG. 12 illustrates a variation of the device 100 which does not include the target object 130. In the illustrated embodiments, the structure 102 itself functions as a target object. As shown in the figure, the structure 102 includes a plurality of markings 810. Marking 810a has a ring configuration, and forms a cross target 820a with marking 810b. Marking 810a also forms a cross target 820b with marking 810c, and a cross target 820c with marking 810d. Marking 810e and marking 810f form a cross target 820d. During use, the markers 108 of the device 100 may be used to determine the position of the device 100, as similarly discussed previously. The positioner 750 may then be used to position the structure 102 such that a reference location 830 associated with the device 100 is at a desired location (e.g., the isocenter of the system 10). In the illustrated embodiments, the reference location 830 is a point intersected by normals of the cross targets 820. Alternatively, the reference location 830 associated with the device 100 may be other locations relative to the device 100. The positioner 750 may also be used to position the structure 102 such that the markings 810 are at desired orientations. After the structure 102 has been desirably positioned and oriented, the lasers 60a-60d are then configured such that their respective laser beams 62a-62d align with the cross targets 820a-820d, as similarly discussed.

In any of the embodiments described herein, the device 100 may not include the plurality of markers 108. In such cases, the position of the structure 102 may be determined using other techniques. For example, the position of the structure 102 may be determined by visual observation or manual measurement. In some cases, the offset between the target object 130 and the target position may be also be determined manually measurement. In such cases, after the offset has been determined, the target object 130 is then placed at the target position based on the offset, either automatically using a positioner or manually.

Computer System Architecture

Figure 13:
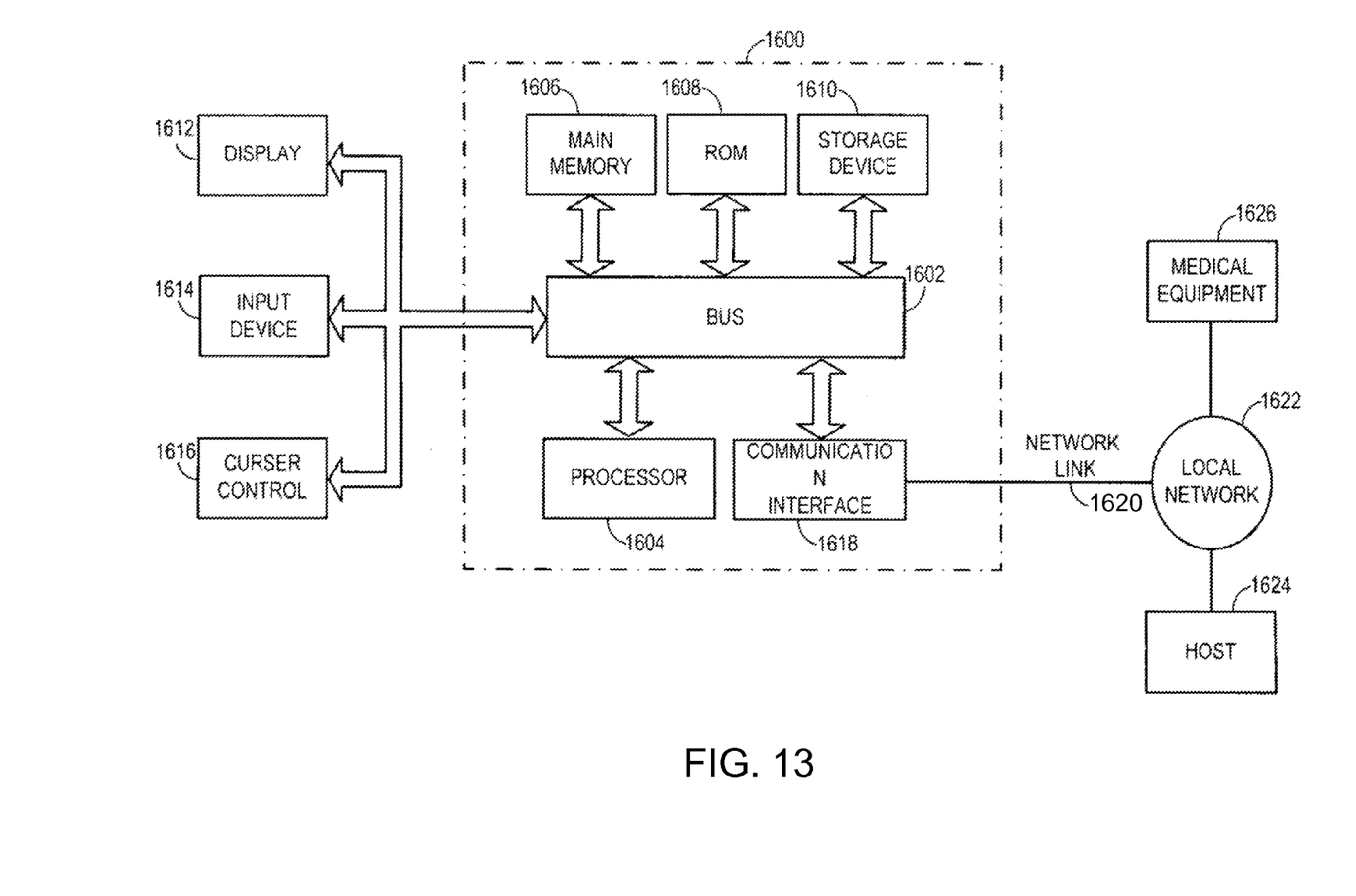
FIG. 13 illustrates a block diagram of a computer system with which embodiments described herein may be implemented.

FIG. 13 is a block diagram illustrating an embodiment of a computer system 1600 that can be used to implement various embodiments of the method described herein. Computer system 1600 includes a bus 1602 or other communication mechanism for communicating information, and a processor 1604 coupled with the bus 1602 for processing information. The processor 1604 may be an example of the processor 54, or alternatively, an example of a component of the processor 54, of FIG. 1. The computer system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The computer system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The computer system 1600 may be coupled via the bus 1602 to a display 1612, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 1612. This input device typically has two degrees of freedom in two axes, a first axis (e.g., x) and a second axis (e.g., y), that allows the device to specify positions in a plane.

In some embodiments, the computer system 1600 can be used to perform various functions described herein. According to some embodiments, such use is provided by computer system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another computer-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "computer-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. Volatile media includes dynamic memory, such as the main memory 1606. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the computer system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The computer system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the computer system 1600, are exemplary forms of carrier waves transporting the information. The computer system 1600 can send messages and receive data, including program code, through the network(s), the network link 1620, and the communication interface 1618.

Although the embodiments of the systems and methods have been described with reference to alignment device that generates laser beam(s), in other embodiments, other types of alignment device may be used with the various embodiments described herein. Also, it should be understood by those skilled in the art that the radiation system 10 needs not be a treatment device, and may be any machine that is capable of generating a radiation beam. In some embodiments, the radiation system 10 may be any types of imaging or optical devices, such as a CT imaging device (e.g., a cone beam CT device), a laminar tomography machine, a MRI machine, a C-arm based x-ray imaging machine, a three dimensional angiography machine, or a PET machine. Also, in other embodiments, any of the calibration devices 100 and/or methods described herein can be used with non-imaging devices, such as a positioner or a treatment machine that has no imaging capability. In further embodiments, any of the calibration devices 100 and/or methods described herein can be used with a machine that has a plurality of radiation sources. For example, the machine can have a first radiation source for delivering diagnostic radiation (e.g., radiation having an energy level in the kilo-electron-volt range), and a second radiation source for delivering treatment radiation (e.g., radiation having an energy level in the mega-electron-volt range). As another example, the machine can also have a plurality of diagnostic radiation sources and/or one or more treatment radiation sources.

Although particular embodiments have been shown and described, it will be understood that they are not intended to limit the present inventions, and it will be obvious to those skilled in the art that various changes and modifications may be made without departing from the spirit and scope of the present inventions. For example, the term "image" as used in this specification includes image data that may be stored in a circuitry or a computer-readable medium, and should not be limited to image data that is displayed visually. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method of calibrating an alignment device, comprising:
   determining a target position associated with a machine;
   determining a position of a calibration device relative to the target position, the calibration device having a structure, a plurality of markers coupled to the structure, and a target object, wherein the position of the calibration device is determined using a matching technique based on a pattern of the plurality of markers as they appear in an image;
   positioning the calibration device based on the determined position of the calibration device relative to the target position; and
   adjusting the alignment device using the target object of the calibration device.

2. The method of claim 1, wherein the target position comprises an isocenter of the machine.

3. The method of claim 1, wherein the machine comprises a radiation machine.

4. The method of claim 1, wherein the alignment device comprises one or a plurality of lasers.

5. The method of claim 1, wherein the target position is determined using a plurality of x-ray images.

6. The method of claim 5, wherein the target position is triangulated from a set of central beam axes.

7. The method of claim 5, wherein the target position is determined using an imaging system that comprises a radiation source.

8. The method of claim 1, wherein the target object comprises a plurality of markings for indicating orientations of the target object.

9. The method of claim 1, wherein the alignment device is configured to emit a laser beam.

10. The method of claim 9, wherein the laser beam has a first plane and a second plane.

11. The method of claim 10, wherein the first plane is approximately perpendicular to the second plane.

12. The method of claim 10, wherein the alignment device is adjusted by adjusting an orientation of the laser beam.

13. The method of claim 1, further comprising adjusting an additional alignment device using the target object, wherein the alignment device and the additional alignment device comprise at least two lasers.

14. The method of claim 1, wherein the machine comprises a treatment radiation machine.

15. The method of claim 1, wherein the act of positioning the calibration device is accomplished automatically using a positioner.

16. The method of claim 1, wherein the markers are embedded within the calibration device, and are configured to be imaged using radiation.

17. The method of claim 1, wherein at least one of the markers is separated from the target object.

18. The method of claim 1, wherein the markers collectively form an asymmetrical configuration.

19. A method of calibrating an alignment device, comprising:
 placing a calibration device next to a radiation machine, the calibration device having a plurality of markers, a first feature on a first side of the calibration device, and a second feature on a second side of the calibration device;
 using a matching technique to determine a position of the calibration device based on a pattern of the plurality of markers as they appear in an image;
 adjusting a first alignment device using the first feature on the first side of the calibration device; and
 adjusting a second alignment device using the second feature on the second side of the calibration device.

20. The method of claim 19, wherein the calibration device comprises a tubular structure and a target object coupled to the tubular structure, wherein the first and second features are on the target object, and wherein the plurality of markers are coupled to the structure.

21. The method of claim 20, further comprising determining a position of the calibration device relative to an isocenter of the radiation machine using the plurality of markers.

22. The method of claim 20, wherein the markers are embedded within the calibration device, and are configured to be imaged using radiation.

23. The method of claim 19, wherein at least one of the markers is separated from the first feature and the second feature.

24. The method of claim 19, wherein the markers collectively form an asymmetrical configuration.

25. A method of calibrating an alignment device, comprising:
 placing a calibration device next to a radiation machine, the calibration device having a plurality of markers, a first feature on a first side of the calibration device, and a second feature on a second side of the calibration device;
 adjusting a first alignment device using the first feature on the first side of the calibration device;
 adjusting a second alignment device using the second feature on the second side of the calibration device; and
 moving the target object relative to the structure so that the target object is at an isocenter of the radiation machine;
 wherein the calibration device comprises a tubular structure and a target object coupled to the tubular structure, wherein the first and second features are on the target object, and wherein the plurality of markers are coupled to the structure.

* * * * *